United States Patent
Joshi et al.

(10) Patent No.: US 8,961,775 B2
(45) Date of Patent: Feb. 24, 2015

(54) HIGH PRODUCTIVITY KOLBE REACTION PROCESS FOR TRANSFORMATION OF FATTY ACIDS DERIVED FROM PLANT OIL AND ANIMAL FAT

(71) Applicant: Altranex Corporation, Scarborough (CA)

(72) Inventors: Chandrashekhar H. Joshi, Kingston (CA); Graham Thomas Thornton Gibson, Kingston (CA); Dzmitry Malevich, Kingston (CA); Michael Glenn Horner, West Roxbury, MA (US)

(73) Assignee: Altranex Corporation (CA)

(*) Notice: Subject to any disclaimer, the term of this patent is extended or adjusted under 35 U.S.C. 154(b) by 0 days.

(21) Appl. No.: 14/331,390

(22) Filed: Jul. 15, 2014

(65) Prior Publication Data

US 2014/0323784 A1    Oct. 30, 2014

Related U.S. Application Data

(63) Continuation-in-part of application No. 13/362,314, filed on Jan. 31, 2012, now abandoned.

(60) Provisional application No. 61/462,381, filed on Feb. 1, 2011.

(51) Int. Cl.
*C25B 3/00* (2006.01)
*C25B 3/10* (2006.01)
(Continued)

(52) U.S. Cl.
CPC ............... *C25B 3/00* (2013.01); *C07C 1/2078* (2013.01); *C10L 1/08* (2013.01); *C10G 3/00* (2013.01); *C10G 3/42* (2013.01); *C10G 3/44* (2013.01); *C10G 3/48* (2013.01); *C25B 3/10* (2013.01); *C10G 45/58* (2013.01); *C10G 45/64* (2013.01); *Y02T 50/678* (2013.01); *Y02E 50/13* (2013.01); *C07C 2521/04* (2013.01); *C07C 2521/08* (2013.01); *C07C 2523/28* (2013.01);
(Continued)

(58) Field of Classification Search
USPC ............................... 585/1; 205/413, 415, 462
See application file for complete search history.

(56) References Cited

U.S. PATENT DOCUMENTS

| | | | |
|---|---|---|---|
| 4,018,844 | A | 4/1977 | Meresz et al. |
| 7,198,710 | B2 | 4/2007 | Miller et al. |

(Continued)

OTHER PUBLICATIONS

B.C.L. Weedon, "Anodic Syntheses With Carboxylic Acids," Quarterly Reviews of Chemical Society, 1952, vol. 6 pp. 380-398.

(Continued)

*Primary Examiner* — Ellen McAvoy
(74) *Attorney, Agent, or Firm* — American Patent Agency PC; Karl P. Dresdner, Jr.; Daniar Hussain

(57) ABSTRACT

Oils from plants and animal fats are hydrolyzed to fatty acids for a Kolbe reaction. The invention relates to a high productivity Kolbe reaction process for electrochemically decarboxylating C4-C28 fatty acids using small amounts of acetic acid to lower anodic passivation voltage and synthesizing C6-C54 hydrocarbons. The C6-C54 undergo olefin metathesis and/or hydroisomerization reaction process to synthesize heavy fuel oil, diesel fuel, kerosene fuel, lubricant base oil, and linear alpha olefin products useful as precursors for polymers, detergents, and other fine chemicals.

20 Claims, 10 Drawing Sheets

(51) Int. Cl.
*C07C 1/207* (2006.01)
*C10L 1/08* (2006.01)
*C10G 3/00* (2006.01)
*C10G 45/58* (2006.01)
*C10G 45/64* (2006.01)

(52) U.S. Cl.
CPC ......... *C07C2523/36* (2013.01); *C07C 2531/12* (2013.01); *C10G 2300/1014* (2013.01); *C10G 2300/1018* (2013.01); *C10G 2300/304* (2013.01); *C10G 2400/22* (2013.01); *C10G 2400/10* (2013.01)
USPC ................ 205/462; 205/413; 205/415; 585/1

(56) References Cited

U.S. PATENT DOCUMENTS

| | | | | |
|---|---|---|---|---|
| 7,459,597 | B2 * | 12/2008 | Koivusalmi et al. | 585/733 |
| 7,582,777 | B2 * | 9/2009 | Bloom | 549/274 |
| 7,928,273 | B2 | 4/2011 | Bradin | |
| 8,067,610 | B2 | 11/2011 | Schrodi | |
| 8,241,881 | B2 * | 8/2012 | Bradin | 435/167 |
| 8,444,845 | B2 * | 5/2013 | Busch | 205/455 |
| 8,481,771 | B2 | 7/2013 | Bradin et al. | |
| 8,506,789 | B2 * | 8/2013 | Bhavaraju et al. | 205/415 |
| 8,518,680 | B2 | 8/2013 | Kuhry et al. | |
| 2008/0161418 | A1 * | 7/2008 | Dierker | 514/762 |
| 2013/0001095 | A1 | 1/2013 | Bhavaraju et al. | |
| 2013/0186770 | A1 * | 7/2013 | Mosby et al. | 205/434 |
| 2013/0284607 | A1 * | 10/2013 | Bhavaraju et al. | 205/440 |
| 2014/0038254 | A1 * | 2/2014 | Kuhry et al. | 435/167 |
| 2014/0154766 | A1 * | 6/2014 | Karanjikar et al. | 435/166 |
| 2014/0257002 | A1 * | 9/2014 | Wang et al. | 585/321 |

OTHER PUBLICATIONS

Sumera, Florentino C. et al., "Diesel Fuel by Kolbe Electrolysis of Potassium Salts of Coconut Fatty Acids and Acetic Acid," Philippine Journal of Science, 1990, vol. 119 (No. 4), pp. 333-345.

Schrodi, Yann et al., "Ruthenium Olefin Metathesis Catalysts for the Ethenolysis of Renewable Feedstocks," Clean Journal, 2008, vol. 36 (8), pp. 669-673.

* cited by examiner

HIGH PRODUCTIVITY KOLBE REACTION PROCESS FOR TRANSFORMATION OF FATTY ACIDS DERIVED FROM PLANT OIL AND ANIMAL FAT

REFERENCE TO RELATED APPLICATIONS

This application is a Continuation-In-Part (CIP) of and claims priority from non-provisional U.S. Ser. No. 13/362,314, filed Jan. 31, 2012, which itself claims priority from provisional U.S. Ser. No. 61/462,381, filed Feb. 1, 2011, the entireties of both of which are hereby incorporated by reference herein.

FIELD OF THE INVENTION

Oils from plants and animal fats are hydrolyzed to fatty acids for a Kolbe reaction. The invention relates to a high productivity Kolbe reaction process for electrochemically decarboxylating C4-C28 fatty acids using small amounts of acetic acid to lower anodic passivation voltage and synthesizing C6-C54 hydrocarbons. The C6-C54 undergo olefin metathesis and/or hydroisomerization reaction process to synthesize heavy fuel oil, diesel fuel, kerosene fuel, lubricant base oil, and linear alpha olefin products useful as precursors for polymers, detergents, and other fine chemicals.

BACKGROUND OF THE INVENTION

The statements in this background section may be useful to an understanding of the invention, but may not constitute prior art.

World-wide production of petroleum is expected to peak around year 2020 and decline thereafter which could cause a global economic decline after 2020. Needed are substitute hydrocarbon sources to petroleum. Inventing alternative, large-scale processes for production of hydrocarbons is needed. These processes need to be economical to be incorporated successfully in free market economies. Research is underway to identify substitute processes and feedstocks for these processes that can be used in large-scale production of needed hydrocarbons. Alternative and renewable feedstocks are being explored for use in economical chemical processes to make hydrocarbons such as fuel oil, diesel fuel, kerosene fuel, lubricant base oil and linear alpha olefins. These particular hydrocarbons are currently obtained from processing petroleum.

Some alternative and renewable feedstocks are plant oils, microbial-produced oils and fatty acids, and animal fats. Because microbial-produced fatty acid feedstocks contain acetates and acetic acid in high molar concentrations of 0.3 M to 0.6 M (Kuhry et al., U.S. Pat. No. 8,518,680), the yield of the aforementioned hydrocarbons (fuel oil, diesel fuel, kerosene fuel, lubricant base oil and linear alpha olefins) are very low which indicates that microbial-produced hydrocarbons are not an economically advantageous feedstock. Other prior art teaches the use of a large wt. % of acetic acid. See for example, Weedon et al. (1952); Sumera and Sadain (1990); and Meresz U.S. Pat. No. 4,018,844 (at Col 2:lines 7-10 and in Example 7 in Table I of Col 3-4 which specifically uses acetic acid and oleic acid in a Kolbe electrolysis reaction). Other prior art such as Bradin U.S. Pat. Nos. 7,928,273 and 8,481,771 which teach processes for the production of biodiesel, gasoline and jet fuel start with vegetable oils or animal fat and employ decarboxylation reactions (thermal or Kolbe) of fatty acids, do not mention any use of acetic acid in the decarboxylation reaction.

Feedstocks such as plant oils and animal fats are triglycerides that can be processed using ester hydrolysis, Kolbe electrolysis, olefin metathesis and hydroisomerization to produce fuel oil, diesel fuel, kerosene fuel, lubricant base oil and linear alpha olefins. Ester hydrolysis may be used to convert oils and fats which contain triglycerides to fatty acids. The fatty acids may be decarboxylated and converted into larger hydrocarbons by Kolbe electrolysis. The alkene hydrocarbons produced from Kolbe electrolysis may be reacted by olefin metathesis using catalysts to redistribute the alkenes by a scission and a regeneration of carbon-carbon double bonds. The linear alkene hydrocarbons formed from olefin metathesis using catalysts may be hydroisomerized to add hydrocarbon branches.

There are many plant oils which can be obtained in large amounts from crop plants. Table 1 below indicates the volumetric (liters and gallons) amounts which can be obtained from crops per hectare or acre. Recycled food oils are also being used as a feedstock to produce the aforementioned hydrocarbons.

TABLE 1

Amounts of Plant Oils That Have Been Obtained From Various Crop Plants

| Crop | liters oil/hectare | US gal/acre |
| --- | --- | --- |
| corn (maize) | 172 | 18 |
| cashew nut | 176 | 19 |
| oats | 217 | 23 |
| lupine | 232 | 25 |
| knead | 273 | 29 |
| calendula | 305 | 33 |
| cotton | 325 | 35 |
| hemp | 363 | 39 |
| soybean | 446 | 48 |
| coffee | 459 | 49 |
| linseed (flax) | 478 | 51 |
| hazelnut | 482 | 51 |
| euphorbia | 524 | 56 |
| pumpkin seed | 534 | 57 |
| coriander | 536 | 57 |
| mustard seed | 572 | 61 |
| camelina | 583 | 62 |
| sesame | 696 | 74 |
| safflower | 779 | 83 |
| rice | 828 | 88 |
| tung oil | 940 | 100 |
| sunflower | 952 | 102 |
| cocoa (cacao) | 1026 | 110 |
| peanut | 1059 | 113 |
| opium poppy | 1163 | 124 |
| rapeseed | 1190 | 127 |
| olive | 1212 | 129 |
| castor bean | 1413 | 151 |
| pecan nut | 1791 | 191 |
| jojoba | 1818 | 194 |
| jatropha | 1892 | 202 |
| macadamia nut | 2246 | 240 |
| brazil nut | 2392 | 255 |
| avocado | 2638 | 282 |
| coconut | 2689 | 287 |
| oil palm | 5950 | 635 |

Plant oils and animal fat (such as beef tallow) contain a mixture of triglycerides which can be hydrolyzed to obtain various fatty acids. Most plant oil-derived and animal fat-derived FFAs typically have 10-20 carbon atoms with zero, one, two or three carbon-carbon double bonds.

The Kolbe electrolysis reaction is a chemical reaction process for the decarboxylation of fatty acids in processes making hydrocarbons. The Kolbe electrolysis reaction process may use a single fatty acid or fatty acid mixtures. A significant renewable source of the fatty acids comes from the hydrolysis of triglycerides of plant oils and animal fats.

There are problems in using the Kolbe electrolysis reaction to produce hydrocarbons from fatty acids. The problems include a development of a passivation voltage (a voltage drop at the Kolbe cell electrodes during the Kolbe electrolysis reaction) which causes need for a higher cell voltage which results in consumption of large quantities of electricity. If plant oils and animal fats are to be an economically viable source from which hydrocarbons may be produced, then the Kolbe electrolysis reaction needs to be improved in terms of its electrical usage efficiency.

In the prior art, improvements have been attempted in the Kolbe electrolysis reaction process by adding a large wt. % of acetic acid to accompany the fatty acids undergoing decarboxylation (see Weedon et al. (1952); Sumera and Sadain (1990); Meresz, U.S. Pat. No. 4,018,844 (at Col 2:lines 7-10 and in Example 7 in Table I of Col 3-4 which specifically uses acetic acid and oleic acid in a Kolbe electrolysis reaction). In the prior art, others practicing the Kolbe reaction do not add any acetic acid at all. Notable examples are the Bradin U.S. Pat. Nos. 7,928,273 and 8,481,771 which teach a production of biodiesel, gasoline and jet fuel from decarboxylation reactions of fatty acids.

Acetic acid is an expensive reagent. Added acetic acid will react in a Kolbe reaction to produce ethane, which is not liquid at room temperature and hence of less interest for particular applications. Production of ethane in this way consumes large amounts of electricity and increases operating costs. In addition, the added acetic acid will react in a Kolbe reaction with the other free fatty acids present in the reaction, such as the fatty acids obtained by hydrolysis of plant oils or animal fats. This side reaction of acetic acid with other fatty acids is Kolbe reaction hetero-coupling. It has been known that the presence of acetic acid will lower the yield of the hydrocarbons that would be produced by the Kolbe reaction process from the feedstock sources (plant oils and animal fats) used to make the fatty acid. Thus there is an important need to improve the Kolbe electrolysis reaction primary hydrocarbon yield and lower wasteful electrical usage by the Kolbe reaction process.

It is against this background that the various embodiments of the present invention were developed.

BRIEF SUMMARY OF THE INVENTION

In preferred embodiments, the present invention involves a method of increasing productivity of a Kolbe electrolysis reaction forming a C6 to C54 hydrocarbon or C6 to C54 hydrocarbons ("one or more C6 to C54 hydrocarbons"), the method comprising: combining a C4-C28 fatty acid or a mixture of C4-C28 fatty acids ("one or more C4-C28 fatty acids") with a solvent and with an amount of acetic acid to create a reaction mixture, wherein the C4-C28 fatty acid or the mixture of C4-C28 fatty acids is between about 80 weight percent to about 99.8 weight percent of the total carboxylic acid weight percent in the solvent, and wherein the amount of the acetic acid is between about 0.2 weight percent to about 20 weight percent of the total carboxylic acid weight percent in the solvent; and performing a high productivity Kolbe electrolysis reaction on the reaction mixture to produce the C6 to C54 hydrocarbon or the C6 to C54 hydrocarbons, wherein the acetic acid in the reaction mixture lowers a passivation voltage of an electrode used in the Kolbe electrolysis reaction. The source of the C4-C28 fatty acid or a mixture of C4-C28 fatty acids may be a plant oil, an animal fat, or a microbial oil.

In other embodiments of the present invention the solvent is a C1 to C4 alcohol, methanol, ethanol, propanol, isopropanol, butanol, water, or a mixture thereof, and the solvent is a mixture which contains between about 0.5 percent to about 50 percent water by volume.

In other embodiments of the present invention the reaction mixture for the Kolbe electrolysis reaction may not be a solution at room temperature.

In other embodiments of the present invention the C4-C28 fatty acid in the solvent or the mixture of C4-C28 fatty acids in the solvent are reacted with a base to form an amount of a salt of the C4-C28 fatty acid in the solvent or the mixture of C4-C28 fatty acids.

In other embodiments of the present invention an electrolyte is added to the reaction mixture to improve electrical conductivity of the Kolbe electrolysis reaction. The electrolyte is selected from the group consisting of a perchlorate salt, a p-toluenesulfonate salt, a tetrafluoroborate salt, and a mixture thereof.

In other embodiments of the present invention the Kolbe electrolysis reaction is conducted at a temperature in the range of about 15° C. to about 100° C.

In other embodiments of the present invention a pressure other than atmospheric pressure may be imposed on the reaction mixture during the Kolbe electrolysis reaction to change a rate of loss of the solvent, the acetic acid, or a C1-C6 volatile fatty acid.

In other embodiments of the present invention current supplied to electrodes is 0.05-1.0 amperes/cm$^2$ area of the electrodes.

In other embodiments of the present invention the reacting surface of the anode electrode is a platinum group metal such as platinum, iridium, palladium, ruthenium, rhodium, or osmium or is a carbon material such as graphite, glassy carbon, baked carbon; or is a mixture of a platinum group metal and a carbon material.

In other embodiments the present invention also involves following the Kolbe electrolysis reaction with an olefin metathesis reaction using a C2-C5 aliphatic alkene or mixtures thereof. The olefin metathesis reaction modifies a chain length of a hydrocarbon and produces a linear alpha olefin or branched hydrocarbons.

In other embodiments the present invention also involves following the Kolbe electrolysis reaction with an ethenolysis reaction using ethene to obtain 1-decene, 1-heptene, 1-butene, 1-octene, 1-hexene and/or 1,4-pentadiene.

In other embodiments the present invention also involves separating the products of the ethenolysis reaction to obtain 1-decene, 1-heptene, 1-butene, 1,4-pentadiene, a diesel fuel, and a heavy fuel oil.

In other embodiments the present invention also involves separating the products from the Kolbe electrolysis reaction which are an amount of diesel fuel and a heavy fuel oil. In other embodiments the present invention also involves hydroisomerizing the heavy fuel oil to produce a lubricant base oil.

In other embodiments of the present invention, the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio of about 2 to about 50.

In other embodiments of the present invention the reaction mixture uses a solvent and a base from a preceding hydrolysis reaction of a triglyceride.

In other embodiments of the present invention the concentration of the C4-C28 fatty acid in the Kolbe electrolysis reaction is between about a 0.01 molar to about a 1 molar.

In preferred embodiments of the present invention the solvent is methanol, ethanol, or isopropanol. In other preferred embodiments of the present invention the weight percent of acetic acid is between 0.2 weight percent to about 5 weight percent.

Other embodiments of the present invention will become apparent from the detailed description of the invention when read in conjunction with the drawings.

BRIEF DESCRIPTION OF THE DRAWINGS

The invention can be further understood by referring to the drawings which represent certain embodiments of the invention.

In FIG. 1a named are sequential hydrolysis and Kolbe electrolysis processes to make hydrocarbons that can be used as a heavy fuel oil. In FIG. 1b named are sequential hydrolysis, Kolbe electrolysis, olefin metathesis, and separation processes to make hydrocarbons suitable for diesel fuel, heavy fuel oil, and shorter linear alpha olefins that can be used as a kerosene fuel or can be used as precursors for advanced polymers, detergents and other fine chemicals. In FIG. 1c named are sequential hydrolysis, Kolbe electrolysis, a separation, and hydroisomerization processes to make hydrocarbons useful as lubricant base oil.

DETAILED DESCRIPTION OF THE INVENTION

The invention relates to the production of hydrocarbon compositions at least substantially oxygen-free and made from sustainable plant oils, animal fats, microbial oils, and combinations thereof. These hydrocarbon compositions can be used in a wide variety of applications. In particular, the hydrocarbon compositions can be employed as fuel for use in passenger and heavy-duty ground transportation vehicles, such as industrial trucks, railroads and the like, cargo and cruise ships and the like, and in aircraft, such as airplanes, helicopters, and the like. Further, the hydrocarbon compositions can be used as a replacement for heating oil to heat houses and the like.

Figure 1A:
FIGS. 1a, 1b, and 1c depict sequential process steps of the invention for making various hydrocarbons.
Figure 1B:
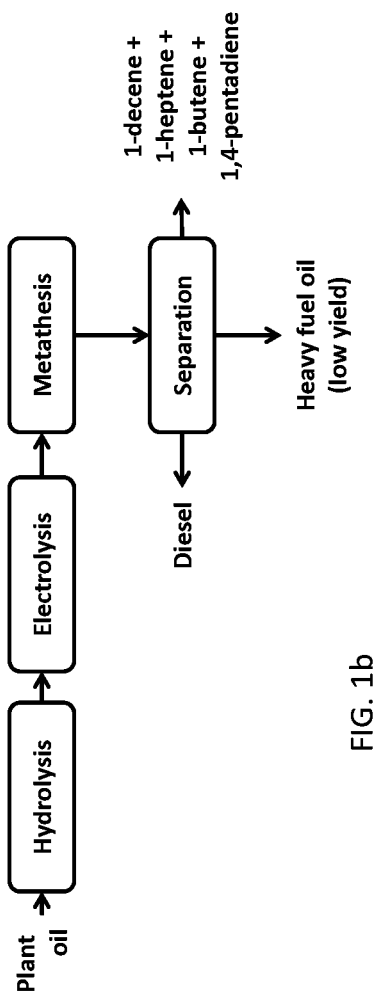
Figure 1C:
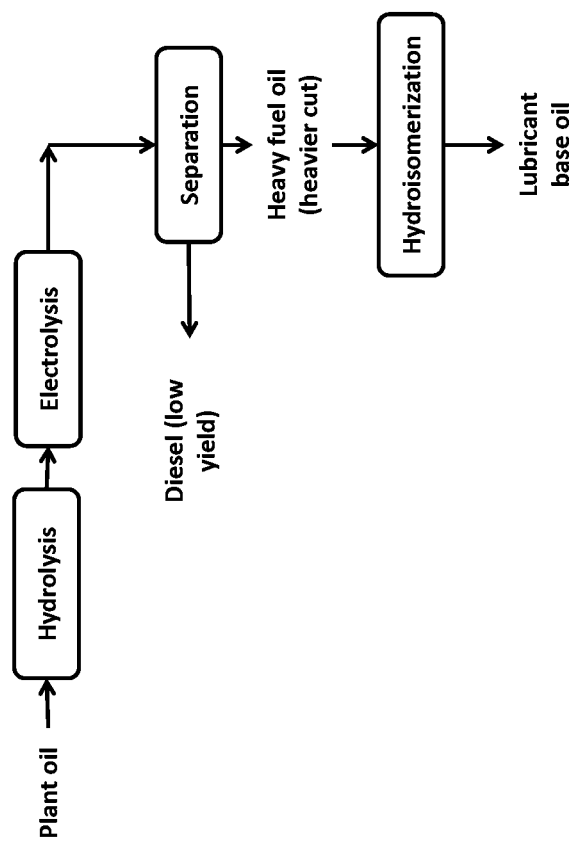

In one aspect, the invention concerns a specialized use of several chemical processes for making heavy fuel oil, diesel fuel, kerosene fuel, lubricant base oil, and linear alpha olefins useful as precursors, from plant oils, animal fats, or combinations thereof. These chemical processes include hydrolysis, Kolbe electrolysis, olefin metathesis and hydroisomerization. FIG. 1a, FIG. 1b, and FIG. 1c depict sequential process steps of the invention for making various hydrocarbons. In FIG. 1a named are sequential hydrolysis and Kolbe electrolysis processes to make hydrocarbons that can be used as a heavy fuel oil. In FIG. 1b named are sequential hydrolysis, Kolbe electrolysis, olefin metathesis, and separation processes to make hydrocarbons suitable for diesel fuel, heavy fuel oil, and shorter linear alpha olefins that can be used as a kerosene fuel or used as precursors for advanced polymers, detergents and other fine chemicals. In FIG. 1c named are sequential hydrolysis, Kolbe electrolysis, separation, and hydroisomerization processes to make hydrocarbons useful as a lubricant base oil.

Two to four of these processes can be combined to make hydrocarbons useful for different applications, including renewable replacements for middle-distillate fuels, heavy fuels, lubricant base oil and linear alpha olefins. Olefin metathesis may be performed prior to hydrolysis, following hydrolysis, or after electrolysis and lead to the same end products. The hydrocarbons produced from these chemical processes are derived from a biological source selected from the group consisting of plant oil, animal fats, microbial oils and combinations thereof and wherein each hydrocarbon composition is at least substantially free of oxygen.

The Kolbe electrolysis reaction is a known useful process for the decarboxylation of fatty acids derived from the hydrolysis of triglycerides of plant oils and animal fats. However, there are problems in using the Kolbe electrolysis reaction to produce hydrocarbons from fatty acids. The problems include a development of a passivation voltage in the Kolbe electrolysis reaction cell which wastes electricity in the Kolbe process.

The hydrolysis can include acid-catalyzed hydrolysis, base-catalyzed hydrolysis or steam hydrolysis and other methods that efficiently convert the plant oil, microbial oil and animal fat into free fatty acids and glycerol. The catalyst used in the hydrolysis reaction can be selected from a wide variety, including acids and bases. Further, the reaction can include the application of heat to improve solubility and accelerate the reaction. The preferred embodiment for large-scale hydrolysis of thermally stable fats and oils is counter-current steam hydrolysis, e.g. the Colgate-Emery process, which efficiently leads to high yields of free fatty acids.

Figure 2:
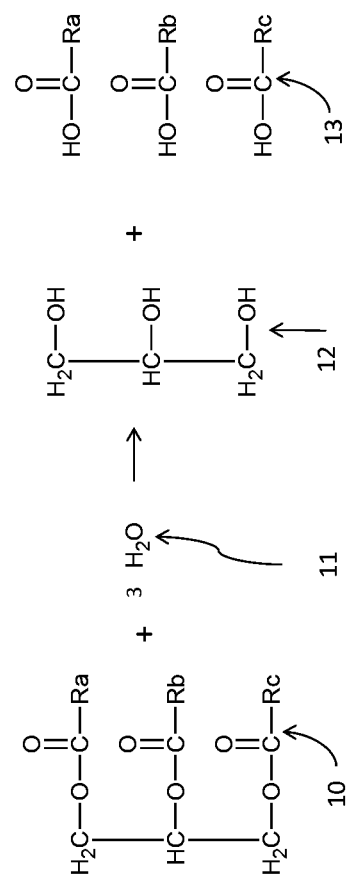
FIG. 2 depicts a hydrolysis reaction of a triglyceride and water to produce free fatty acids and glycerol which is a process step which may be practiced in accordance with certain embodiments of the invention.

FIG. 2 depicts a chemical structure diagram to show a hydrolysis reaction of a triglyceride and water to produce free fatty acids and glycerol which is a process step which may be practiced in accordance with certain embodiments of the invention. As shown in FIG. 2, a triglyceride 10 is reacted with water 11 to produce glycerol 12 and fatty acids 13. In the reaction example in FIG. 2, the triglyceride 10 includes substituents $R_a$, $R_b$, and $R_c$. A triglyceride is the prevalent component of plant or animal fats. Typical plant oils are a mixture of triglycerides that have commonly three linear hydrocarbon chains as depicted in FIG. 2 by substituents $R_a$, $R_b$, and $R_c$. The free fatty acids following hydrolysis of typical plant triglycerides have 10, 12, 14, 16, 18, 20, 22, or 24 carbons or a mixture of these carbon numbers. The present invention may also use a monoglyceride or a diglyceride. The substituents $R_a$, $R_b$, and $R_c$ of the glyceride do not need to have all three substituents be fatty acid esters, e.g., one glyceryl substituent may contain alternative functional groups that include the elements phosphorus, oxygen, or nitrogen.

For some embodiments of the present invention the free fatty acids produced from the hydrolysis reaction contain various even numbers of carbon atoms, from 4 to 28, in a single unbranched chain. Most of the bonds between the carbon atoms in the single fatty acid chain will be single carbon-carbon bonds. When the bonds in the fatty acid chain are all single bonds, then the free fatty acid is called a saturated fatty acid. In unsaturated fatty acids some bonds between adjacent carbon atoms are double bonds. In polyunsaturated fatty acids, the fatty acid chain has multiple double carbon-carbon bonds.

Figure 3:
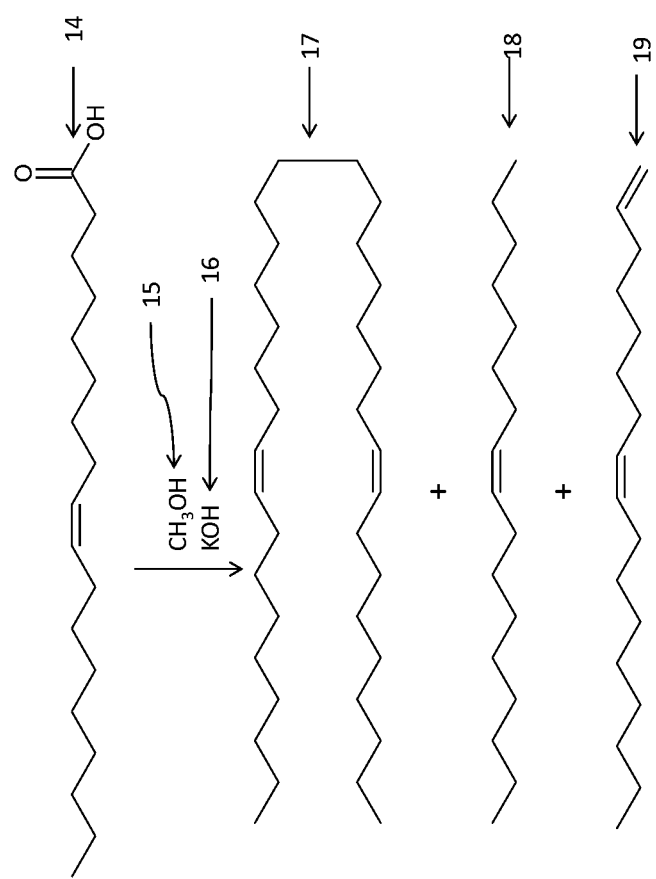
FIG. 3 depicts a Kolbe electrolysis reaction of oleic acid, a free fatty acid, with methanol and potassium hydroxide into three different linear hydrocarbons which is a process step which may be practiced in accordance with certain embodiments of the invention.

Kolbe electrolysis is a reaction to electrochemically oxidize carboxylic acids to produce alkanes, alkenes, alkane-containing products, alkene-containing products and mixtures thereof. The reaction proceeds through radical intermediates to yield products based on dimerization of these radicals, such that an n-carbon acid will combine with an m-carbon acid to form an alkane and/or alkene of length (m+n−2) carbons along with two carbon dioxide molecules and one hydrogen molecule. The radical intermediates also lead to shorter alkane and/or alkene products by disproportionation. In the Kolbe electrolysis, only the carboxyl groups participate in the reaction and any unsaturation that may be present in the fatty acid chain is preserved in the final product. FIG. 3 shows a Kolbe electrolysis reaction in accordance with certain embodiments of the invention. As shown in FIG. 3, oleic acid 14 is reacted by Kolbe electrolysis in solvent methanol 15 in the presence of base potassium hydroxide 16 to produce (cis,cis)-9,25-tetratriacontadiene 17, in addition to small amounts of disproportionation products 18 and 19.

In Kolbe electrolysis, homocoupling is the reaction of two similar free fatty acids creating a symmetrical hydrocarbon product, and heterocoupling is the reaction between two different free fatty acids. The mixture of fatty acids derived from the hydrolysis of a plant oil, microbial oil, animal fat, or combination thereof undergo both homocoupling reactions and heterocoupling reactions in Kolbe electrolysis. The resulting hydrocarbons constitute a range of chain lengths and molecular weights, including those derived from disproportionation of the radical intermediates, which are in the range suitable for diesel fuel, heavy fuel oil and lubricant base oil.

The productivity of the Kolbe reaction is critical to the commercial success of producing hydrocarbons from free fatty acids. The efficiency of the use of electrical current is measured by the current yield, which is the percentage of current used for the reaction of interest (Kolbe electrolysis) relative to the total current applied. For commercial use, however, the cost of electrical power is as important as the current yield, and as such the cell voltage is another critical parameter. The inventors have defined a new term, "productivity", defined herein as the product yield divided by the electrical energy required, in units such as g/kWh. By optimizing this figure, a high productivity is obtained resulting in lower production costs. In the case of Kolbe electrolysis, the specified product for the calculation of productivity is defined as all the hydrocarbons of interest for a specific application derived from the substrate fatty acids.

Products of the hydrolysis reaction which may be present in the Kolbe electrolysis reaction solution may include some unreacted triglycerides, diglycerides, monoglycerides, or glycerol depending upon the feedstock. In the present invention preferably the hydrolysis reaction includes a significant aqueous phase and is designed so that all of the feedstock fats and oils are hydrolyzed into a water-insoluble free fatty acids phase which floats on top of the aqueous phase. Preferably the glycerol byproduct of the hydrolysis reaction fully dissolves into the aqueous phase. In one embodiment of the present invention, the hydrolysis is performed with a base catalyst in a C1-C3 alcohol. It may be advantageous to retain the solvent and/or base from the hydrolysis reaction, for the Kolbe electrolysis reaction.

Preferred solvents for the Kolbe electrolysis include C1-C3 alcohols. More preferably the solvents employed in the Kolbe electrolysis reaction are methanol or ethanol or a mixture of C1-C3 alcohols thereof. The Kolbe reaction is tolerant to the presence of water, and water may be present in this reaction in amounts up to 40% by volume. In certain embodiments, solubility of reaction components may be improved in a solvent system which comprises a mixture of alcohol and water. More preferably the solvent system for the Kolbe reaction comprises about 2% to 50%, about 5% to 45%, about 10% to 40% or about 20% to 30% by volume (water in ethanol).

The initial reaction mixture for the Kolbe electrolysis reaction may not be a solution (with the feedstock and other components dissolved) at room temperature (22° C.). In some embodiments of the present invention, the Kolbe electrolysis may be performed at temperatures below or above room temperature. Preferably the Kolbe electrolysis reaction is conducted at a temperature in the range of about 15° C. to about 100° C. Higher pressures than atmospheric pressure may be employed to prevent loss of the solvent or a boiling over of the reaction mixture. In instances where a volatile fatty acid is present following the hydrolysis reaction, in some embodiments of the present invention the volatile fatty acid may be allowed to volatilize by lowering the pressure following or during the hydrolysis reaction in order to eliminate volatile fatty acids from being present during the Kolbe electrolysis reaction.

In the Kolbe electrolysis reaction, a base may be added to partially convert the carboxylic acid group of the fatty acids to a carboxylate salt prior to initiating or during the Kolbe reaction undergoing electrolysis. In some embodiments of the present invention preferably the fatty acids will be neutralized by ranges from about 10 to 80, 20 to 60, or 30 to 50 percent. In this case the percent means the concentration of the base in molar units relative to the total carboxylic acid molar concentration. The preferred bases for the neutralization of the fatty acids are hydroxide, alkoxide or carbonate salts of sodium or potassium. Amine bases may also be used. Anions other than the carboxylates of the substrate carboxylic acids may interfere and should not be present. In some embodiments of the present invention an electrolyte may be added to the Kolbe reaction mixture to increase the Kolbe reaction mixture electrical conductivity. Preferably an electrolyte to improve the Kolbe reaction mixture electrical conductivity is selected from the group consisting of perchlorate, p-toluenesulfonate or tetrafluoroborate salts of sodium or tetraalkylammonium or a mixture thereof. An increase in mixture conductivity means the same as a decrease in mixture resistivity.

The preferred material of the cathode in Kolbe electrolysis is stainless steel, nickel, or graphite, although other suitable materials may also be used, including platinum or gold. The preferred material of the anode is platinum, at least at the reacting surface of the anode. The anode may be a foil or plate consisting of the preferred anode material or the anode material may be plated on or affixed to a support material such as titanium, graphite, or glass, with the preferred support material being titanium. For example, an anode consisting of a 1 mm-thick titanium plate electroplated with 1 micrometer of platinum was used for the Kolbe electrolysis of oleic acid to give a productivity value equivalent to that found using a platinum foil anode. Other materials may also be used as the anode, including non-porous graphite, gold or palladium.

The preferred current density, defined as the current supplied to the electrode divided by the active surface area of the electrode, applied to the Kolbe electrolysis is 0.05-1.0, 0.1-0.4 or 0.1-0.3 $A/cm^2$.

Figure 4:
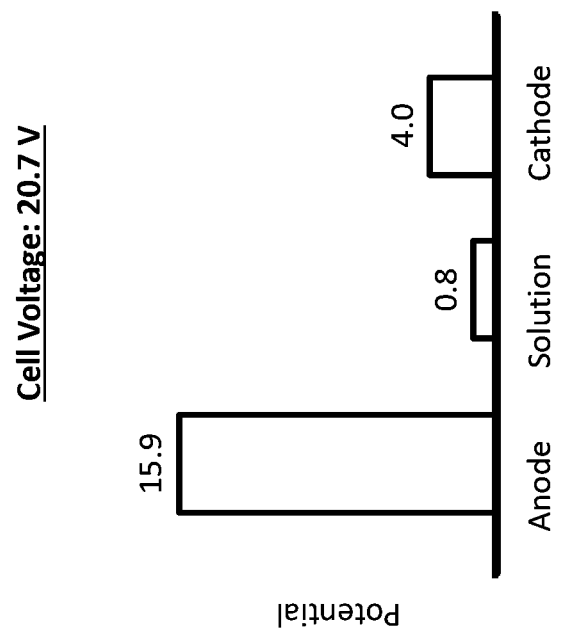
FIG. 4 depicts an example of the relative contributions of solution resistance, cathodic potential, and anodic potential to the cell voltage occurring during a Kolbe electrolysis reaction of oleic acid in the presence of sodium hydroxide in 70% ethanol/water by volume.

As shown in the Kolbe reaction example depicted in FIG. 4 the net (overall) cell voltage (voltage means electrical potential) of a Kolbe electrolysis reaction cell can be 20.7 volts. The overall cell voltage (also termed the net cell voltage) is a measureable cell voltage between the anode electrode and the cathode electrode. In some embodiments of the present invention as exemplified in Kolbe electrolysis reactions of Examples 1, 2, 3, 4, 5, 6 and 7, the measured cell voltage is between about 12.5 volts to about 33 volts depending upon reaction conditions which include the type of triglyceride, the amount and type of base, the electrical current density, the reaction temperature, and the molar percent acetic acid (less than 10% gives a higher productivity and yield).

This overall cell voltage (cell voltage or net cell voltage) drop measured between the immersed anode and cathode electrodes is believed to be comprised of several voltage drops occurring in the Kolbe electrolysis reaction cells. The cell voltage drop may be due to several factors. These factors in FIG. 4 for example include:

(a) an anode potential drop of 15.9 volts in the example of FIG. 4 which in part is caused by the Kolbe electrolysis reaction with fatty acids and which may change during the Kolbe reaction due to a development of an overvoltage drop on the external immersed electrode surfaces which in part may be caused by an anode electrode passivation process;

(b) a cathode potential drop of 4.0 V in the example of FIG. 4 which may change during the Kolbe reaction due to a development of an overvoltage drop on the external immersed electrode surfaces which in part may be caused by a cathode passivation process;

(c) a Kolbe reaction cell solution voltage drop of 0.8 volts due to solution resistivity and current flow between the electrodes (which according the Ohm's law may be calculated as the mathematical product of the measured solution resistance between the electrodes before the Kolbe reaction solution and the current flow between the electrodes.

The passivation process at the immersed electrodes during the Kolbe reaction is a chemical process problem which needs to be controlled when possible. Passivation may be found to be a voltage-dependent, a current-dependent, or a solution resistivity-dependent factor. The causes and means to modulate electrode passivation may require controlling many Kolbe reaction conditions, and thus controlling passivation may be problematic.

For example, in some embodiments of the present invention, the net cell voltage needs to be minimized to make the Kolbe process economical which means not wasting the electricity going into the Kolbe electrolysis reaction. The net cell voltage is a voltage that can be current-dependent and would be cell resistivity dependent. The electrical current at an adequate electrochemical voltage driving force in the Kolbe reaction cell causes Kolbe electrolysis reaction of free fatty acids to have an adequate yield and reasonable reaction duration. For example, for some embodiments of the present invention, preferably the current flow ranges between about 0.05 to about 0.50 amperes/$cm^2$ across the conductive surfaces of the anode and cathode during the Kolbe reaction to have a reaction yield of about 95% and a reaction duration of about one hour. In Example 4, the Kolbe cell reaction solution was a 70% ethanol-30% water solution and the fatty acid was 0.5 M oleic acid that has been neutralized by 40 mole percent with sodium hydroxide. The Kolbe electrodes had a 1.5 mm solution gap and the Kolbe reaction was operated with a current density of 0.2 amperes/$cm^2$ of electrode area.

In the present invention, passivation at the electrodes employed during the Kolbe electrolysis was considered a wasteful electrical usage problem that needed to be reduced to make commercially practicing the present invention an economically viable process for creating hydrocarbons. However, at the same time for some embodiments of the present invention, the yield of the desired Kolbe hydrocarbon product needed to be a high yield. It was found that the amount of electrode voltage passivation could be reduced by including small amounts of acetic acid or sodium acetate to the Kolbe reaction solution, the acetate or acetic acid being less than 10 mole percent relative to the molar concentration of the fatty acid and which did not greatly reduce the Kolbe reaction yield.

As mentioned by the example in FIG. 4, there are multiple factors which impact the overall cell voltage of a Kolbe electrolysis reaction. The electrochemical potentials for the anodic and cathodic reactions are expected to contribute about 2.5 V and <2 V, respectively, so that the remainder of the voltage measured for the anode and cathode come from electrode passivation. Thus, in the example of FIG. 4, the anodic overvoltage constitutes the majority of the overall cell voltage of 20.7 V. Electrical resistance of the solution can be reduced by adding a supporting electrolyte to the solution, although in example FIG. 4 solution resistance voltage drop is not a significant contributor, accounting for only 0.55 V/millimeter (mm) electrode gap distance. In the example depicted in FIG. 4 there is only a 1.5 millimeter electrode gap.

Electrode passivation has been found to be greater when the fatty acid substrate in the Kolbe reaction is an unsaturated fatty acid with polyunsaturated fatty acids leading to greater passivation than mono-saturated fatty acids. A reduction in the effects of passivation, and thus cell voltage, is considered to have an important direct impact on the productivity of the reaction.

Figure 5:
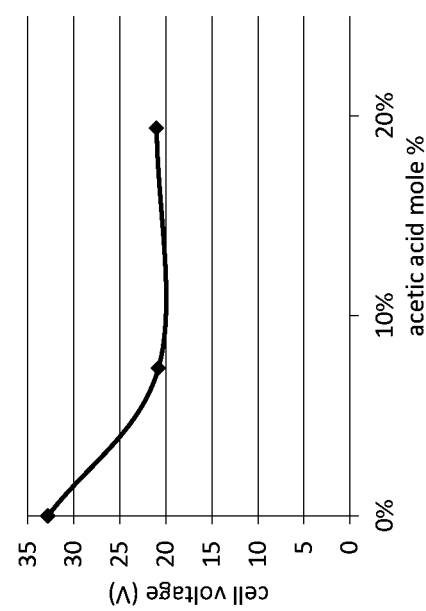
FIG. 5 depicts a graph plotting the dependence of the cell voltage of a Kolbe electrolysis reaction of oleic acid as a function of the mole percent of acetic acid added.
Figure 6:
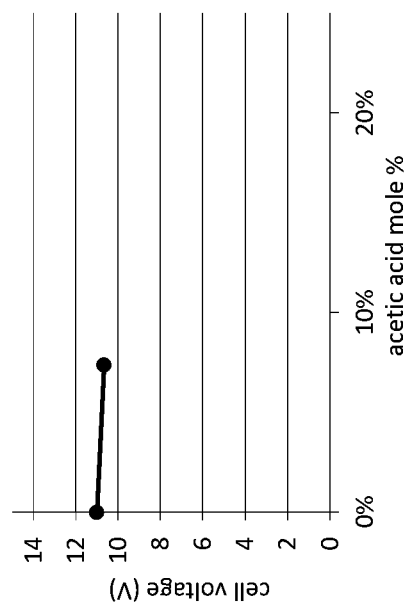
FIG. 6 depicts a graph plotting the dependence of the cell voltage of a Kolbe electrolysis reaction of stearic acid as a function of the mole percent of acetic acid added.

In one aspect of the invention, the productivity of the Kolbe electrolysis reaction is improved by adding a small molar percent acetic acid to the reaction mixture containing a mixture of fatty acids derived from a plant oil, an animal fat, microbial oil or a combination thereof. The addition of acetic acid substantially reduced electrode passivation leading to lower cell voltage and increased productivity. Surprisingly, even small amounts of added acetic acid lead to a considerable reduction in cell voltage, and the dependence of cell voltage on the amount of added acetic acid is non-linear. FIG. 5 shows a graph which plots the dependence of cell voltage on the mole % of acetic acid mixed with oleic acid. From FIG. 5 it can be seen that only 7.4 mole % acetic acid lowers the voltage from 32.8 V in the case of 100% oleic acid, to 21.0 V, or to 64% of original. This translates to an increase in productivity (mass per electrical energy used) of 56%. In contrast, for stearic acid, the saturated equivalent of oleic acid, electrode passivation has significantly less impact on the cell voltage. FIG. 6 shows a graph which plots the dependence of cell voltage on the mole % of acetic acid mixed with stearic acid. From FIG. 6 it can be seen that 7.4 mole % acetic acid has very little effect on the cell voltage, lowering it from 11.0

V in the case of 100% stearic acid to 10.7 V, or to 97% of original. Because passivation was not the main contributor to cell voltage, the acetic acid did not make much of a difference, further confirming a) that acetic acid is acting to ameliorate electrode passivation and b) that solution conductivity, as would be increased by an the addition of acetic acid, does not have much effect on cell voltage for this reaction.

The productivity for the Kolbe electrolysis of the mixture, in g/kW·h, can thus be calculated as: $P=M\cdot 1000/(i\cdot V\cdot t)$, where M is the mass of products of interest generated, in g; i is the electrical current supplied to the electrochemical cell, in amperes; V is the voltage applied to the electrochemical cell, in volts; and t is the time over which current has been supplied, in hours. It follows from the productivity formula that in order to maximize productivity, the incorporation of acetic acid into the product has to be minimized to maximize the M value. Therefore, in the preferred embodiment of this invention the electrochemical conversion of acetic acid is minimized by using a low content of acetic acid in the solution. This use of acetic acid is in contrast to the prior art, which describes the deliberate Kolbe heterocoupling reaction of fatty acids with short-chain acids such as acetic acid (see, for example Meresz et al., U.S. Pat. No. 3,932,616), wherein the preferred embodiment is to use a large molar excess of acetic acid in order to maximize the conversion of fatty acids to heterocoupling products with acetic acid.

In accordance with certain embodiments, the invention can include olefin metathesis with ethene (i.e., ethenolysis) or other lower alkene, such as propene, to modify the chain length of the hydrocarbons and to produce linear alpha olefins. In certain embodiments, branched hydrocarbons can be produced, for example, by use of alkenes having two alkyl substituents on one double-bonded carbon, such as 2-methylpropene (isobutylene), in place of ethene in the olefin metathesis reaction. When employed, olefin metathesis can be performed prior to the hydrolysis and Kolbe electrolysis or in-between the hydrolysis and Kolbe electrolysis or, in the preferred embodiment, after Kolbe electrolysis.

Metathesis is a process involving the exchange of a bond (or bonds) between similar interacting chemical species such that the bonding affiliations in the products are closely similar or identical to those in the reactants. Olefin metathesis reactions operate specifically at carbon-carbon double bonds. In such reactions, an olefin described generically as A=A can react with a second olefin, B=B, to yield a cross-over product, A=B. If multiple unsaturated species are available, all possible combinations of cross-over products can typically be obtained, with the product ratio determined largely by the concentrations of the reactants. Internal olefins can be reacted with ethene to produce smaller olefins. This reaction is referred to as ethenolysis, which produces alpha olefins (compounds with terminal double bonds). In certain embodiments, ethenolysis can be performed on the hydrocarbons derived from the Kolbe electrolysis, leading to the linear alpha olefins 1-decene, 1-heptene, 1-butene and 1,4-pentadiene, among others. These linear alpha olefins are useful as precursors to polymers, detergents, and other fine chemicals. In particular, 1-decene, and to a lesser extent 1-heptene and 1-butene, are useful in the production of poly alpha olefins, specifically useful for synthetic lubricants, comprising Group IV of the API classification of lubricant base oils. Alternatively, the shorter-chain hydrocarbons produced in the olefin metathesis reaction may be used as fuel, either left mixed with longer hydrocarbons to improve the cold-flow properties of the mixture of hydrocarbons or separated, e.g. by distillation, and used as a fuel with good cold-flow properties, e.g. as kerosene would be used. In certain embodiments, wherein the olefin metathesis reaction is performed on the plant oil, animal fat or combination thereof, the hydrocarbon product distribution following hydrolysis and Kolbe electrolysis on the mixture would be the same as that wherein the olefin metathesis reaction is performed on the hydrocarbon products of the Kolbe electrolysis reaction.

The olefin metathesis reaction requires a transition metal catalyst. The catalyst may be either heterogeneous or homogeneous with the reaction medium. Common homogeneous catalysts include metal alkylidene complexes as have been described by Schrock, Grubbs, and others. Common heterogeneous metathesis catalysts include rhenium and molybdenum oxides supported on a silica or alumina carrier.

Figure 7:
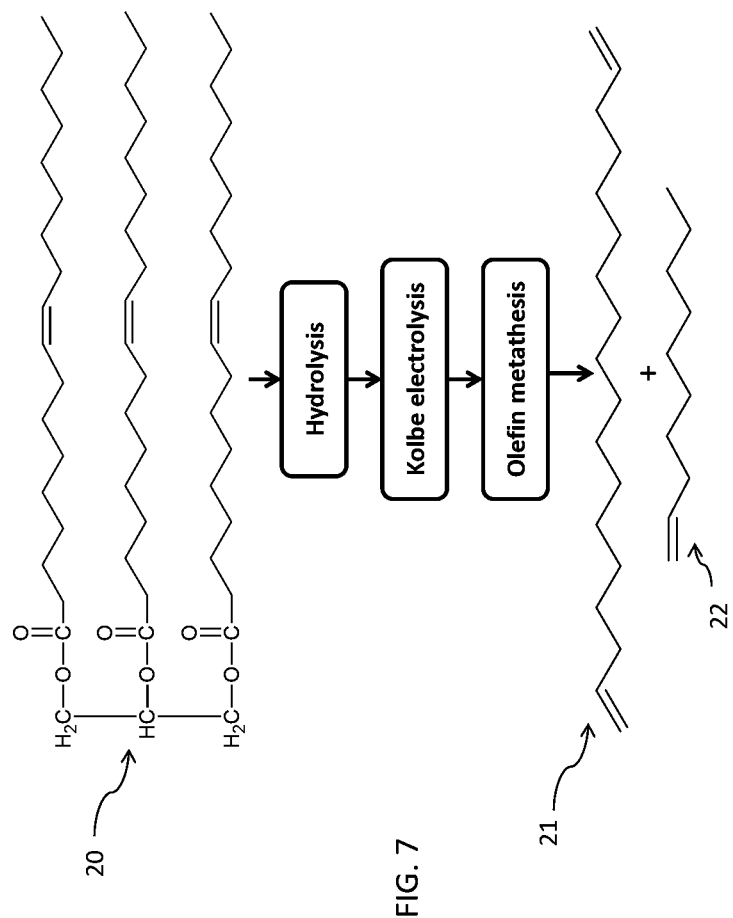
FIG. 7 depicts a series of three chemical reactions; hydrolysis, Kolbe electrolysis and olefin metathesis using as a feedstock the oil, glyceryl trioleate, to produce a mixture of two linear hydrocarbons in accordance with certain embodiments of the invention.
Figure 8:
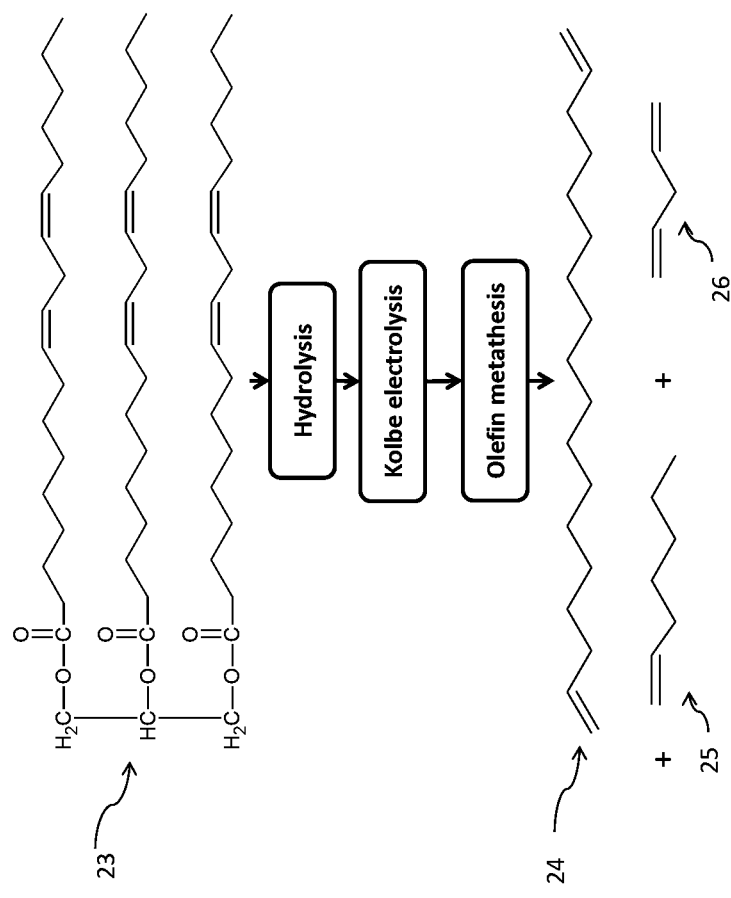
FIG. 8 depicts a series of three chemical reactions; hydrolysis, Kolbe electrolysis and olefin metathesis using as a feedstock the oil, glyceryl trioleate, to produce a mixture of three linear hydrocarbons in accordance with certain embodiments of the invention.

FIG. 7 and FIG. 8 show a process for producing hydrocarbon fuel from hydrocarbons produced by Kolbe electrolysis in accordance with certain embodiments of the invention. As shown in FIG. 7, glyceryl trioleate 20 (a triglyceride) is subjected to hydrolysis, Kolbe electrolysis, and olefin metathesis (ethenolysis) to produce the linear alpha olefins 1,17-octadecadiene 21, and 1-decene 22. As shown in FIG. 8, glyceryl trilinoleate 23 is subjected to hydrolysis, Kolbe electrolysis, and olefin metathesis (ethenolysis) to produce the linear alpha olefins 1,17-octadecadiene 24, 1-heptene 25 and 1,4-pentadiene 26. The composition of linear alpha olefins derived from the olefin metathesis of hydrocarbons derived from oils and fats can be predicted by the average composition of fatty acids in the oil or fat, as the narrow range of fatty acids leads to a narrow range of possible linear alpha olefins. Therefore, the yield of particular desired linear alpha olefins can be improved by careful selection of plant oil, microbial oil, animal fat or combinations thereof wherein the fatty acids that lead to the desired linear alpha olefin are present in high concentration.

In accordance with certain embodiments of the invention, hydroisomerization can be used on the hydrocarbon product of the Kolbe electrolysis reaction to modify the properties of the hydrocarbon such that it is more suitable for use as lubricant base oil. The hydroisomerization reaction is performed in the presence of hydrogen gas and a catalyst having a metal component to catalyze skeletal isomerization, yielding saturated, branched hydrocarbons having about the same molecular weight as the substrate hydrocarbons. The resulting hydrocarbon material is more stable to oxidation and is more fluid at lower temperatures, which are desirable properties. In a preferred hydroisomerization reaction process of the present invention, the catalyst is a silica-alumina zeolite containing impregnated platinum, the temperature is 250-400° C., the pressure is 10-400 bar, and the $H_2$:hydrocarbon ratio is 2-50.

EXAMPLE 1

Kolbe Electrolysis Reaction of Beef Tallow-Derived Fatty Acids 9.44 parts fatty acids derived from the hydrolysis of beef tallow was added to 89.69 parts methanol; 0.87 parts potassium hydroxide was added to the mixture, which was then heated to 52° C. in a water-jacketed vessel, obtaining a clear solution. An electrolysis cell, consisting of platinum foil anode and nickel cathode separated by 1.5 mm gap, was immersed into the solution. A constant electrical current density of 0.2 A $cm^{-2}$ was applied. Within 1 hour, hydrocarbon product separated from the reaction mixture and accumulated at the bottom of the reactor, comprising coupled Kolbe electrolysis products and disproportionation products.

EXAMPLE 2

Kolbe Electrolysis Reaction of Oleic Fatty Acid in Presence of 0.6 Wt. % Acetic Acid of Total Acids 16.49 parts oleic acid, 0.10 parts acetic acid (0.6 wt. % of total acid), and 0.98 parts sodium hydroxide was dissolved in 59.47 parts ethanol and 22.96 parts water, which was then heated to 50° C. in a water jacketed vessel. An electrolysis cell, consisting of platinum foil anode and platinum foil cathode separated by 1.5 mm gap, was immersed into the solution. A constant electrical current density of 0.2 A cm$^{-2}$ was applied. After 50 minutes of electrolysis an aliquot of the reaction mixture was acidified and extracted into hexane, which was then analyzed by gas chromatography to calculate current yield and productivity (see Table 2).

EXAMPLE 3

Kolbe Electrolysis Reaction of Oleic Fatty Acid at a Moderate Electrical Current Density 16.26 parts oleic acid and 1.15 parts sodium hydroxide was dissolved in 53.52 parts ethanol and 29.07 parts water, which was then heated to 50° C. in a water-jacketed vessel. An electrolysis cell, consisting of platinum foil anode and platinum foil cathode separated by 1.5 mm gap, was immersed into the solution. A constant electrical current density of 0.1 A cm$^{-2}$ was applied. After 100 minutes of electrolysis an aliquot of the reaction mixture was acidified and extracted into hexane, which was then analyzed by gas chromatography to calculate current yield and productivity (see Table 2).

EXAMPLE 4

Kolbe Electrolysis Reaction of Oleic Fatty Acid at a High Electrical Current Density The solution of Example 3 was electrolyzed in the same manner as in Example 3, except that the current density was 0.3 A cm$^{-2}$ and the reaction time was 33.3 minutes.

EXAMPLE 5

Kolbe Electrolysis of Oleic Fatty Acid 16.32 parts oleic acid and 0.97 parts sodium hydroxide was dissolved in 53.60 parts ethanol and 29.11 parts water, which was then electrolyzed in the same manner as the solution in Example 2.

EXAMPLE 6

Kolbe Electrolysis of More Neutralized Oleic Fatty Acid 16.19 parts oleic acid and 2.25 parts sodium hydroxide was dissolved in 52.85 parts ethanol and 28.71 parts water, which was then electrolyzed in the same manner as the solution in Example 2.

EXAMPLE 7

Kolbe Electrolysis of Oleic Fatty Acid with a Large Acetic Acid Concentration 15.71 parts oleic acid, 6.68 parts acetic acid (29.8 wt. % of total acid), and 3.34 parts sodium hydroxide was dissolved in 48.13 parts ethanol and 26.14 parts water, which was then heated to 40° C. in a water jacketed vessel. An electrolysis cell, consisting of platinum foil anode and platinum foil cathode separated by 1.5 mm gap, was immersed into the solution. A constant electrical current density of 0.25 A cm$^{-2}$ was applied. After 40 minutes of electrolysis an aliquot of the reaction mixture was acidified and extracted into hexane, which was then analyzed by gas chromatography to calculate current yield and productivity (see Table 2).

As disclosed in the above Examples and in Table 2 data for the Examples, the Kolbe electrolysis reaction of Example 2 which has only 0.7 wt. % of total acid as acetic acid. Thus, Example 2 Kolbe reaction employed a very low molar ratio of acetic acid to oleic acid (a 1:164.9 molar ratio) and the Kolbe reaction current yield of 54.9%. More notably in the presence of trace amounts of less than 1% acetic acid, the Kolbe reaction of Example 2 has a high productivity calculated to be 340 g/kWh. The 50 minute Kolbe reaction of Example 2 produces a high productivity and also a low overall cell voltage of 14.3 volts.

In marked contrast to Example 2, the productivity of Example 7 is inferior despite having 29.8 wt. % of total acid as acetic acid. Example 7 uses 42.7 times more acetic acid than is used in Example 2. In terms of molar ratios, Example 7 uses a molar ratio of acetic acid to oleic acid equal to 15.71:6.68 or a 70%:30% molar percent ratio. The more than 42 fold higher wt. % of acetic acid in Example 7 compared to Example 2 results in a 6.8 fold lower productivity, 50 g/kWh versus 340 g/kWh.

The results of Example 2 with very low molar percent acetic acid in a Kolbe reaction of oleic fatty acid (0.6:99.4 molar percent acetic acid:oleic fatty acid) versus the results of Example 7 with a 70:30 molar percent acetic acid:oleic acid are surprising and contradict the prior art teachings of Kuhry U.S. Pat. No. 8,518,680. For example, Kuhry Example Bio-3 and Table B-1 used 102.4 mM (millimolar) acetic acid to 153.2 total mM acid or a molar percent ratio of 0.66:0.34 molar percent acetic acid:fatty acids (see Col 20:lines 39 to-end of Col. 20). Thus Kuhry teaches using a very high molar fraction. This is also a consequence of Kuhry's use of a source of fatty acids derived from biomass fermentation from which acetic acid is a major acid.

In addition, Bhavaraju et al. in US Patent Publication 2013/0001095 on page 3: paragraph 22 teaches Kolbe electrolysis reactions containing up to 26 wt. % sodium acetate which is a product of a sodium hydroxide neutralized acid solution, which may be advantageous in providing a high electrolyte conductivity (low Kolbe cell solution resistivity).

As depicted in the Kolbe reaction cell example of FIG. 4 of the present invention, the voltage drop in the Kolbe reaction solution is only 0.8 volts of a 20.7 volt cell (4% of the Kolbe cell voltage example of FIG. 4 of the present invention). Thus for the present invention high acetic acid would insignificantly improve electricity usage (increase productivity g/kWh). Thus the conductivity teaching of Bhavaraju is not relevant to the process of present invention that employs less than 1 wt % acetic acid. Additionally, Example 7 of the present invention, which employed 29.8 wt. % acetic acid, gave inferior results that indicate that the Kolbe reaction process of the present invention is markedly different than the Kolbe reaction process of Bhavaraju.

Similarly, the prior art teaches the use of a large wt. % of acetic acid (see Weedon et al. (1952); Sumera and Sadain (1990); Meresz U.S. Pat. No. 4,018,844 (at Col 2:lines 7-10 and in Example 7 in Table I of Col 3-4 which specifically uses acetic acid and oleic acid in a Kolbe electrolysis reaction). Notably Bradin, U.S. Pat. Nos. 7,928,273 and 8,481,771, which teach biodiesel, gasoline and jet fuel production from decarboxylation reactions of fatty acids, however, they do not mention using acetic acid at all.

TABLE 2

Current yield and productivity data for experiments described in Examples 2-7

| | Current yield (%) | Cell voltage (V) | Productivity (g/kWh) |
|---|---|---|---|
| Example 2 | 54.9 | 14.3 | 340.0 |
| Example 3 | 66.7 | 24.2 | 244.7 |
| Example 4 | 61.7 | 32.0 | 170.9 |
| Example 5 | 79.5 | 27.9 | 252.5 |
| Example 6 | 29.0 | 12.5 | 206.4 |
| Example 7 | 5.0 | 12.6 | 50.1 |

EXAMPLE 8

Ethenolysis of Oleic Acid-Derived Kolbe Reaction Products in Dichloromethane, an Olefin Metathesis Process 3.00 parts hydrocarbons from the Kolbe electrolysis of oleic acid were added to a vessel; 0.62 parts catalyst (commercial Grubbs' $2^{nd}$ generation metathesis catalyst) was dissolved in 96.38 parts dichloromethane and the resulting solution was added to the vessel. The vessel was sealed and pressurized with ethene to 52 bar. The reaction was stirred at ambient temperature for 2 hours, at which time the vessel was depressurized and ethyl vinyl ether was added to quench the reaction. The contents were passed through silica and analyzed by GC-MS. Results indicate that 1-decene and 1,17-octadecadiene, the only linear alpha olefins expected from a substrate derived entirely from oleic acid, were the only ethenolysis products present in the reaction mixture.

EXAMPLE 9

Hydroisomerization of a Straight Chain Hydrocarbon Product of a Kolbe Electrolysis Reaction to Add Side-Chains to the Straight Chain Hydrocarbon The product from the Kolbe electrolysis of a fatty acid mixture is subjected to vacuum distillation to remove hydrocarbons with atmospheric boiling points <250° C. The residue is passed through a fixed bed reactor containing a catalyst comprising an acidic, porous silica-alumina support and 0.5 weight percent platinum loaded onto the support by incipient wetness impregnation. The reactor is heated to 300° C. and pressurized with hydrogen gas to 50 bar. The liquid hourly space velocity is 1 $h^{-1}$ and the hydrogen:substrate feed ratio is 10:1.

Some embodiments of the present invention are a method of increasing productivity of a Kolbe electrolysis reaction forming a C6 to C54 hydrocarbon or C6 to C54 hydrocarbons, the method comprising:

combining a C4-C28 fatty acid or a mixture of C4-C28 fatty acids with a solvent and with an amount of acetic acid to create a reaction mixture, wherein the C4-C28 fatty acid or the mixture of C4-C28 fatty acids is between about 80 weight percent about 99.8 weight percent of the total carboxylic acid weight percent in the solvent, and wherein the amount of the acetic acid is between about 0.2 weight percent to about 20 weight percent of the total carboxylic acid weight percent in the solvent; and performing a high productivity Kolbe electrolysis reaction on the reaction mixture to produce the C6 to C54 hydrocarbon or the C6 to C54 hydrocarbons, wherein the acetic acid in the reaction mixture lowers a passivation voltage of an electrode used in the Kolbe electrolysis reaction. The source of the C4-C28 fatty acid or a mixture of C4-C28 fatty acids may be a plant oil, an animal fat, or a microbial oil.

Other embodiments of the present invention include wherein the solvent is a C1- to C4 alcohol, methanol, ethanol, propanol, isopropanol, butanol, water, or a mixture thereof, and wherein the solvent is a mixture which contains between about 0.5 percent to about 50 percent water by volume.

Other embodiments of the present invention include wherein the reaction mixture for the Kolbe electrolysis reaction may not be a solution at room temperature.

Other embodiments of the present invention include wherein the C4-C28 fatty acid in the solvent or the mixture of C4-C28 fatty acids in the solvent are reacted with a base to form an amount of a salt of the C4-C28 fatty acid in the solvent or the mixture of C4-C28 fatty acids.

Other embodiments of the present invention include wherein an electrolyte is added to the reaction mixture to improve electrical conductivity of the Kolbe electrolysis reaction, and wherein the electrolyte is selected from the group consisting of a perchlorate salt, a p-toluenesulfonate salt, a tetrafluoroborate salt, and a mixture thereof.

Other embodiments of the present invention include wherein the Kolbe electrolysis reaction is conducted at a temperature in the range of about 15° C. to about 100° C.

Other embodiments of the present invention include wherein a pressure other than atmospheric pressure may be imposed on the reaction mixture during the Kolbe electrolysis reaction to change a rate of loss of the solvent, the acetic acid, or a C1-C6 volatile fatty acid.

Other embodiments of the present invention include wherein current supplied to electrodes is 0.05-1.0 amperes/$cm^2$ area of the electrodes Other embodiments of the present invention include wherein a reacting surface of an anode electrode is a platinum group metal selected from the group consisting of a platinum, a iridium, a palladium, a ruthenium, a rhodium, an osmium, and a combination thereof; or is a carbon material selected from the group consisting of a graphite, a glassy carbon, a baked carbon, and a combination thereof; or is a mixture of one or more of the metals of the platinum group metals and the one or more of the carbon materials.

Other embodiments of the present invention further comprise following the Kolbe electrolysis reaction with an olefin metathesis reaction using a C2-C5 aliphatic alkene or mixtures thereof, wherein the olefin metathesis reaction modifies a chain length of a hydrocarbon and produces a linear alpha olefin or branched hydrocarbons.

Other embodiments of the present invention further comprise following the Kolbe electrolysis reaction with an ethenolysis reaction using ethene to obtain 1-decene, 1-heptene, 1-butene, 1-octene, 1-hexene and/or 1,4-pentadiene.

Other embodiments of the present invention further comprise separating the products of the ethenolysis reaction to obtain 1-decene, 1-heptene, 1-butene, 1-octene, 1-hexene, 1,4-pentadiene, a diesel fuel, and a heavy fuel oil.

Other embodiments of the present invention further comprise separating the products from the Kolbe electrolysis reaction which are an amount of diesel fuel and a heavy fuel oil, and further comprising hydroisomerizing the heavy fuel oil to produce a lubricant base oil.

Other embodiments of the present invention include wherein the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio of about 2 to about 50.

Other embodiments of the present invention include wherein a reaction mixture has an amount of a hydrolysis solvent and a hydrolysis base from a preceding hydrolysis reaction of a feedstock triglyceride.

Other embodiments of the present invention include wherein the one or more C4-C28 fatty acid in the Kolbe electrolysis reaction is at a concentration of between about 0.01 molar to about 1 molar.

Other embodiments of the present invention include wherein the solvent is methanol. Other embodiments of the present invention include wherein the solvent is ethanol. Other embodiments of the present invention include wherein the solvent is isopropanol. Other embodiments of the present invention include wherein the weight percent of acetic acid is between 0.2 weight percent to about 5 weight percent.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Whereas particular embodiments of the invention have been described herein for purposes of illustration, numerous variations of the details may be made without departing from the invention as set forth in the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a tip" includes a plurality of tips. Thus, for example, a reference to "a method" includes one or more methods, and/or steps of the type described herein and/or which will become apparent to those persons skilled in the art upon reading this disclosure.

What is claimed is:

1. A method of increasing productivity of a Kolbe electrolysis reaction forming one or more C6 to C54 hydrocarbons, the method comprising:
   combining one or more C4-C28 fatty acids with a solvent and with an amount of acetic acid to create a reaction mixture,
   wherein the one or more C4-C28 fatty acids is between about 80 weight percent to about 99.8 weight percent of a total carboxylic acid weight percent in the solvent, and
   wherein the amount of the acetic acid is between about 0.2 weight percent to about 20 weight percent of the total carboxylic acid weight percent in the solvent; and
   performing a Kolbe electrolysis reaction on the reaction mixture to produce the one or more C6 to C54 hydrocarbons,
   wherein the acetic acid in the reaction mixture lowers a passivation voltage of an electrode used in the Kolbe electrolysis reaction.

2. The method of claim 1, wherein the solvent is a C1 to C4 alcohol, methanol, ethanol, propanol, isopropanol, butanol, water, or a mixture thereof, and wherein the solvent is a mixture which contains between about 0.5 percent to about 50 percent water by volume.

3. The method of claim 1, wherein the reaction mixture for the Kolbe electrolysis reaction is not a solution at room temperature.

4. The method of claim 1, wherein the one or more C4-C28 fatty acids in the solvent are reacted with a base to form an amount of a salt of the one or more C4-C28 fatty acids.

5. The method of claim 1, wherein an electrolyte is added to the reaction mixture to improve electrical conductivity of the Kolbe electrolysis reaction, and wherein the electrolyte is selected from the group consisting of a perchlorate salt, a p-toluenesulfonate salt, a tetrafluoroborate salt, and mixtures thereof 6. The method of claim 1, wherein the Kolbe electrolysis reaction is conducted at a temperature in a range of about 15° C. to about 100° C.

7. The method of claim 1, wherein a pressure is imposed on the reaction mixture during the Kolbe electrolysis reaction to change a rate of loss of the solvent, or of the acetic acid, or of a C1-C6 volatile fatty acid.

8. The method of claim 1, wherein an electrical current supplied to electrodes is 0.05-1.0 amperes per $cm^2$ area of the electrodes.

9. The method of claim 1, wherein a reacting surface of an anode electrode is a platinum group metal selected from the group consisting of a platinum, a iridium, a palladium, a ruthenium, a rhodium, an osmium, and a combination thereof; or is a carbon material selected from the group consisting of a graphite, a glassy carbon, a baked carbon, and a combination thereof or is a mixture of one or more of the metals of the platinum group metals and the one or more of the carbon materials.

10. The method of claim 1, further comprising:
    following the Kolbe electrolysis reaction with an olefin metathesis reaction using a C2-C5 aliphatic alkene or a mixture of C2-C5 aliphatic alkenes, wherein the olefin metathesis reaction modifies a chain length of the hydrocarbon.

11. The method of claim 1, further comprising:
    following the Kolbe electrolysis reaction with an ethenolysis reaction using ethene to obtain 1-decene, 1-heptene, 1-butene, 1-octene, 1-hexene, or 1,4-pentadiene.

12. The method of claim 11, further comprising:
    separating the products of the ethenolysis reaction to obtain 1-decene, 1-heptene, 1-butene, 1-octene, 1-hexene, 1,4-pentadiene, a diesel fuel, and a heavy fuel oil.

13. The method of claim 1, further comprising:
    hydroisomerizing at least some of the products from the Kolbe electrolysis reaction to produce a lubricant base oil.

14. The method of claim 13, wherein the hydroisomerization reaction uses a catalyst which is a silica/alumina-based zeolite containing impregnated platinum, a reaction temperature between about 250° C. to about 400° C., a reaction pressure between about 10 bar to about 400 bar, and a hydrogen gas to a hydrocarbon ratio of about 2 to about 50.

15. The method of claim 1, wherein a reaction mixture has an amount of a hydrolysis solvent and a hydrolysis base from a preceding hydrolysis reaction of a feedstock triglyceride.

16. The method of claim 1, wherein the one or more C4-C28 fatty acids in the Kolbe electrolysis reaction is at a concentration of between about 0.01 molar to about 1 molar.

17. The method of claim 1, wherein the solvent is methanol.

18. The method of claim 1, wherein the solvent is ethanol.

19. The method of claim 1, wherein the solvent is a mixture of methanol and ethanol.

20. The method of claim 1, wherein the weight percent of acetic acid is between 0.2 weight percent to about 5 weight percent.

* * * * *